United States Patent
Edwin et al.

[11] Patent Number: 6,053,943
[45] Date of Patent: Apr. 25, 2000

[54] ENDOLUMINAL GRAFT WITH INTEGRAL STRUCTURAL SUPPORT AND METHOD FOR MAKING SAME

[75] Inventors: Tarun J. Edwin, Tempe; Christopher E. Banas, Mesa, both of Ariz.

[73] Assignee: Impra, Inc., Tempe, Ariz.

[21] Appl. No.: 09/077,533

[22] PCT Filed: Dec. 8, 1995

[86] PCT No.: PCT/US95/16497

§ 371 Date: May 28, 1998

§ 102(e) Date: May 28, 1998

[87] PCT Pub. No.: WO97/21401

PCT Pub. Date: Jun. 19, 1997

[51] Int. Cl.⁷ .................................. A61F 2/04; A61F 2/06
[52] U.S. Cl. ........................ 623/1.25; 623/12; 623/1.44; 623/1.13; 600/36
[58] Field of Search .............................. 623/1, 12; 600/36

[56] References Cited

U.S. PATENT DOCUMENTS

| | | | |
|---|---|---|---|
| Re. 31,618 | 7/1984 | Mano et al. ................................. | 623/1 |
| 3,105,492 | 10/1963 | Jeckel . | |
| 3,304,557 | 2/1967 | Polansky . | |
| 4,580,568 | 4/1986 | Gianturco . | |
| 4,588,461 | 5/1986 | Braun .......................................... | 623/1 |
| 4,604,762 | 8/1986 | Robinson . | |
| 4,629,458 | 12/1986 | Pinchuk . | |
| 4,733,665 | 3/1988 | Palmaz . | |
| 4,747,849 | 5/1988 | Galtier ...................................... | 623/12 |
| 4,767,418 | 8/1988 | Deininger et al. . | |
| 4,776,337 | 10/1988 | Palmaz . | |
| 4,816,339 | 3/1989 | Tu et al. . | |
| 4,850,999 | 7/1989 | Planck . | |
| 4,857,069 | 8/1989 | Kira . | |
| 4,969,896 | 11/1990 | Shors . | |
| 5,061,275 | 10/1991 | Wallstén et al. . | |
| 5,084,065 | 1/1992 | Weldon et al. . | |
| 5,102,417 | 4/1992 | Palmaz . | |
| 5,116,360 | 5/1992 | Pinchuk et al. . | |
| 5,116,365 | 5/1992 | Hillstead ..................................... | 623/1 |
| 5,167,614 | 12/1992 | Tessmann et al. . | |
| 5,192,307 | 3/1993 | Wall . | |
| 5,195,984 | 3/1993 | Schatz . | |
| 5,219,361 | 6/1993 | von Recum et al. . | |
| 5,236,446 | 8/1993 | Dumon . | |
| 5,282,823 | 2/1994 | Schwartz et al. ........................ | 606/198 |
| 5,282,824 | 2/1994 | Gianturco . | |
| 5,282,847 | 2/1994 | Trescony et al. . | |
| 5,282,860 | 2/1994 | Matsuno et al. . | |
| 5,334,201 | 8/1994 | Cowan . | |
| 5,556,426 | 9/1996 | Popadiuk et al. .......................... | 623/1 |
| 5,607,478 | 3/1997 | Lentz et al. ............................... | 623/12 |
| 5,609,624 | 3/1997 | Kalis ........................................... | 623/1 |
| 5,749,880 | 5/1998 | Banas et al. ............................. | 606/198 |
| 5,851,232 | 12/1998 | Lois .............................................. | 623/1 |
| 5,871,536 | 2/1999 | Lazarus ...................................... | 623/1 |
| 5,871,537 | 2/1999 | Holman et al. ............................ | 621/1 |
| 5,873,906 | 2/1999 | Lau et al. .................................... | 623/1 |

Primary Examiner—David H. Willse
Assistant Examiner—Suzette Jackson
Attorney, Agent, or Firm—Graham & James LLP

[57] ABSTRACT

A structurally supported graft (10) having a support structure (26) with strain relief sections (30) contained with an internal surface, an external surface, or a wall thickness of a tubular graft member (12). The structurally supported graft (10) may include a beading element (24) which is co-extruded with the support structure (26) having strain relief sections (30) and spiraled about the tubular graft (10). The support structure (26) includes differing types of strain relief sections (30) which are capable of allowing for the longitudinal and radial expansion of the structurally supported graft (10), respectively. The strain relief sections (30) may also include unconnected ends which form outwardly protruding barbs (62) upon expansion of the structurally supported graft within a blood vessel or body lumen. The method for making the structurally supported graft includes selecting or preparing a support structure with strain relief sections, co-extruding the structural support with a beading element, forming a spiral about the tubular graft with the co-extruded structure, and securing the co-extruded structure to the tubular graft.

33 Claims, 5 Drawing Sheets

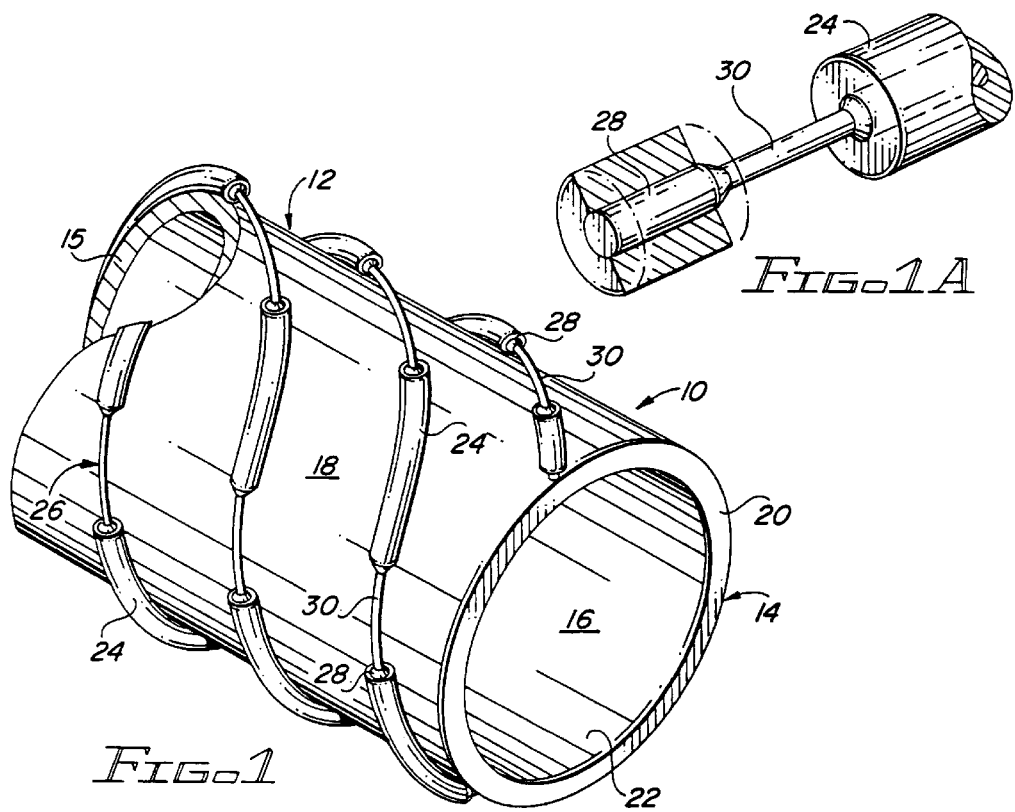
FIG. 1
FIG. 1A
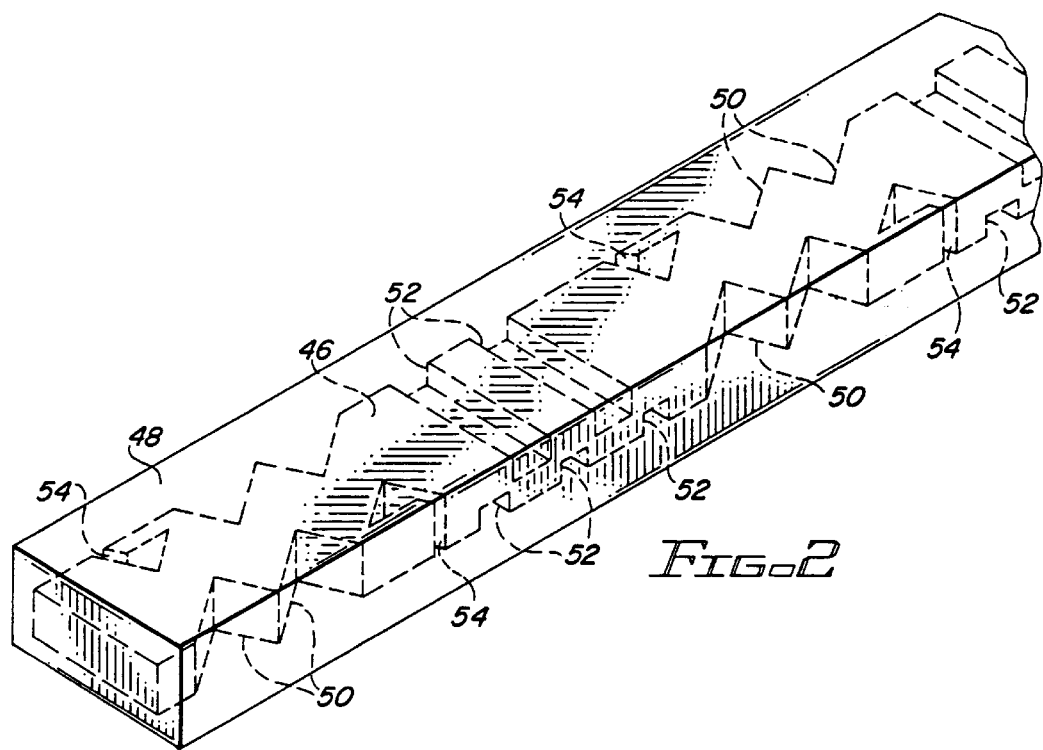
FIG. 2

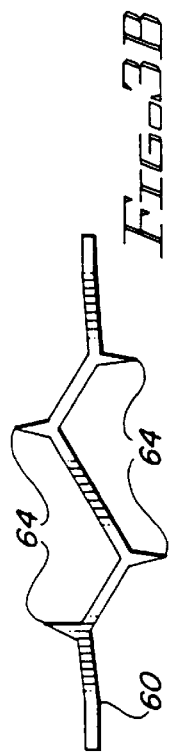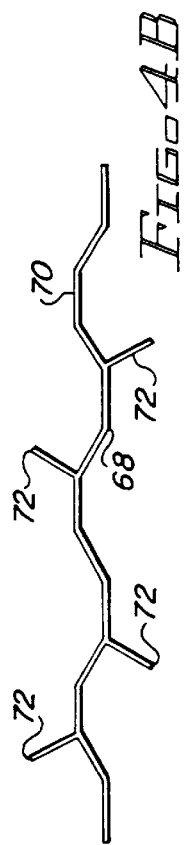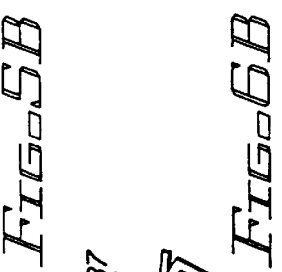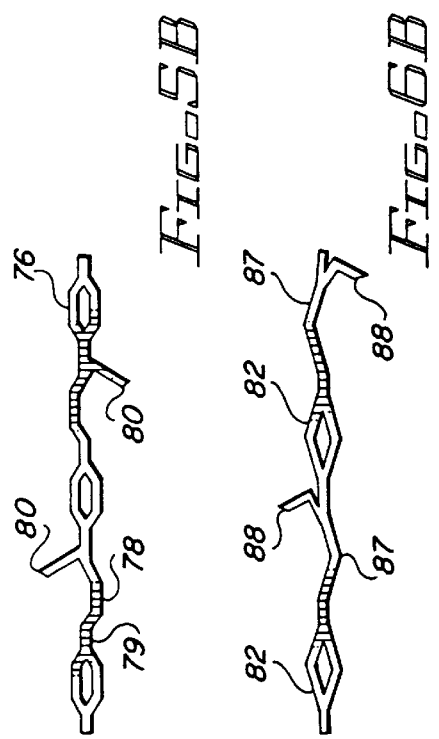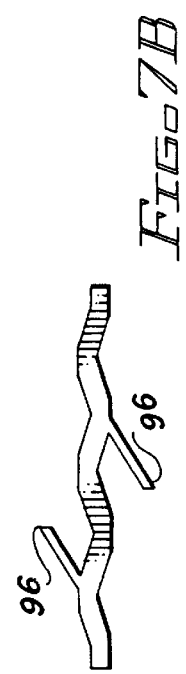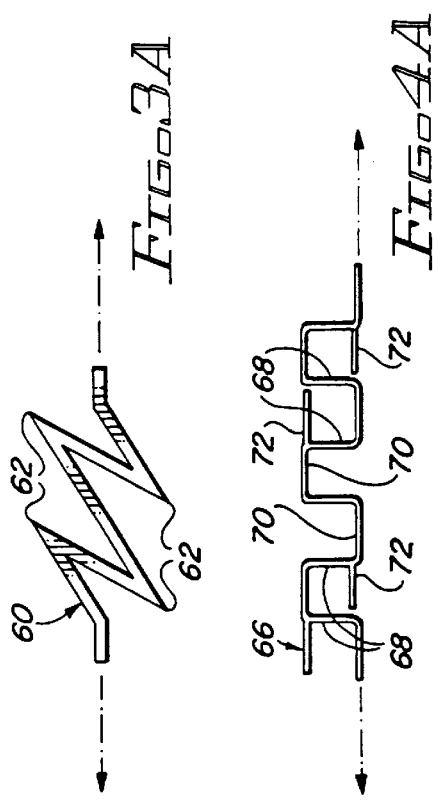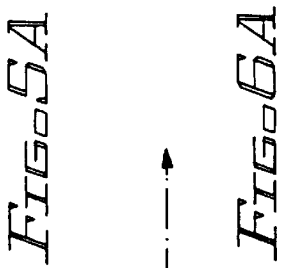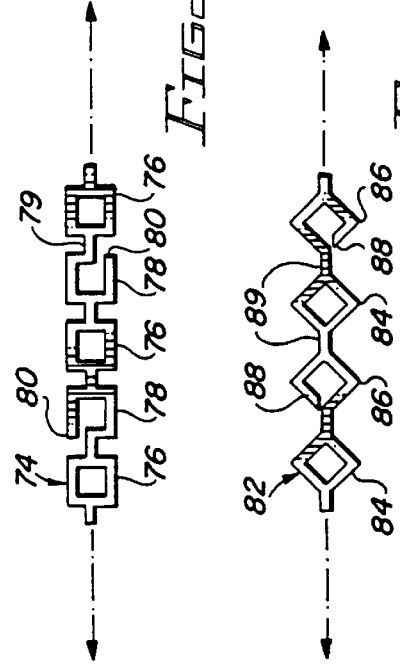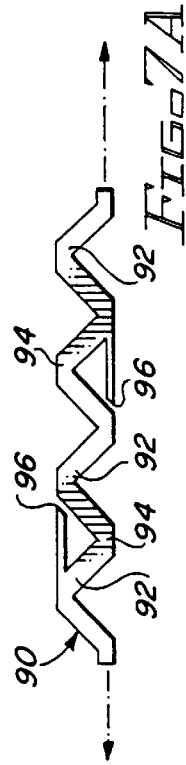

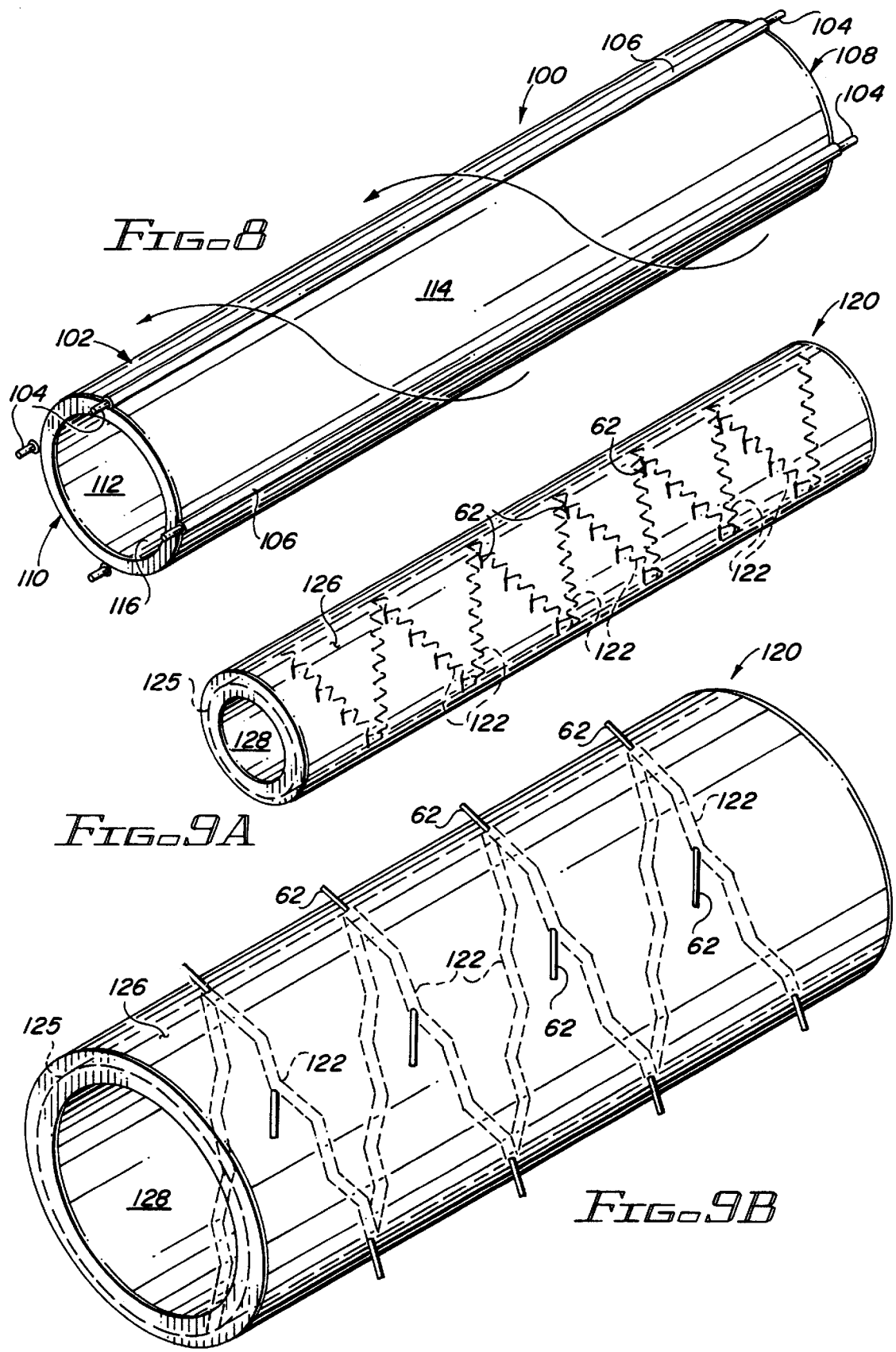

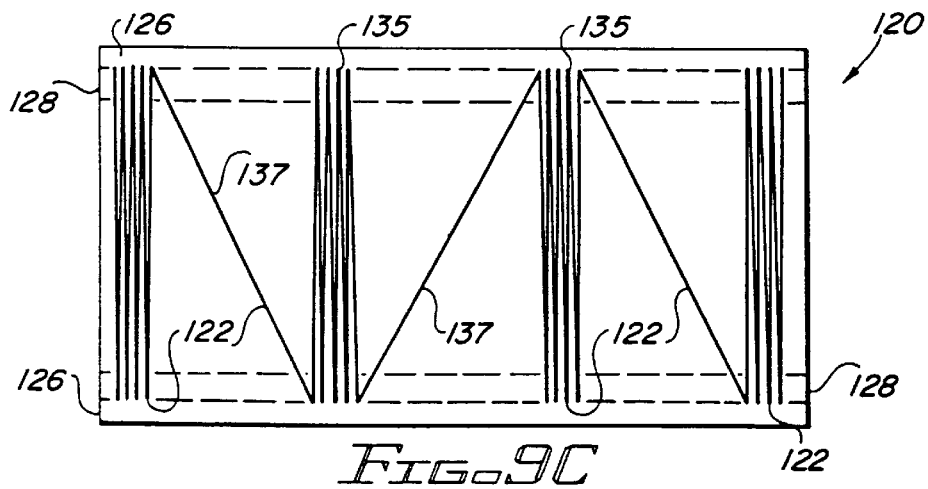
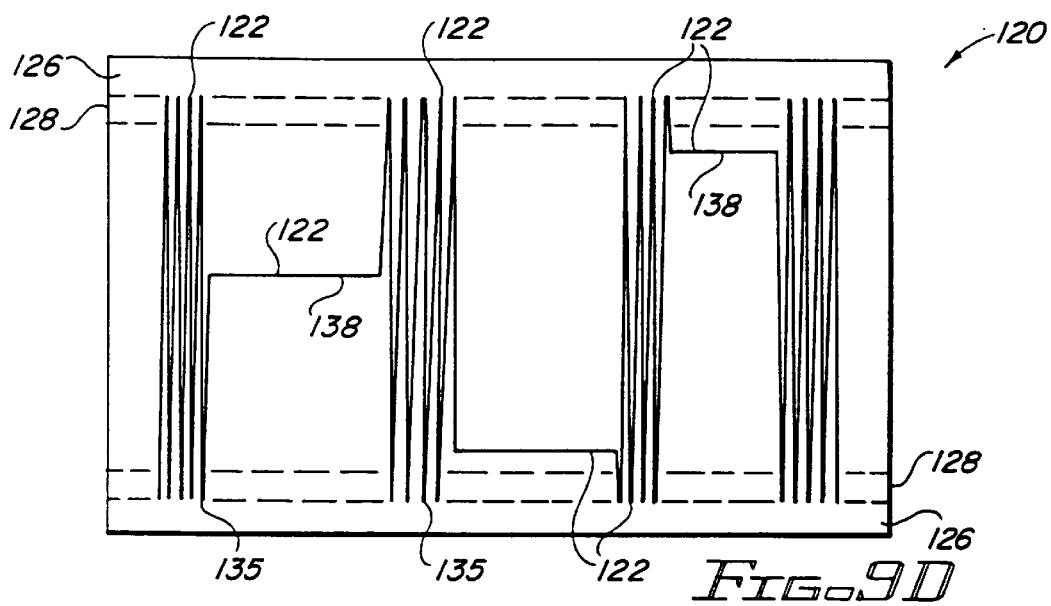
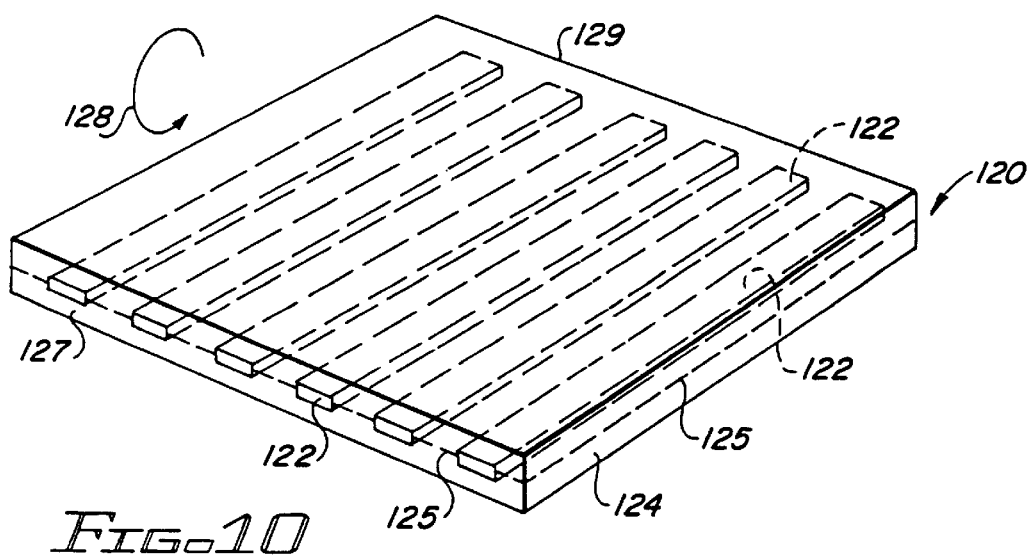

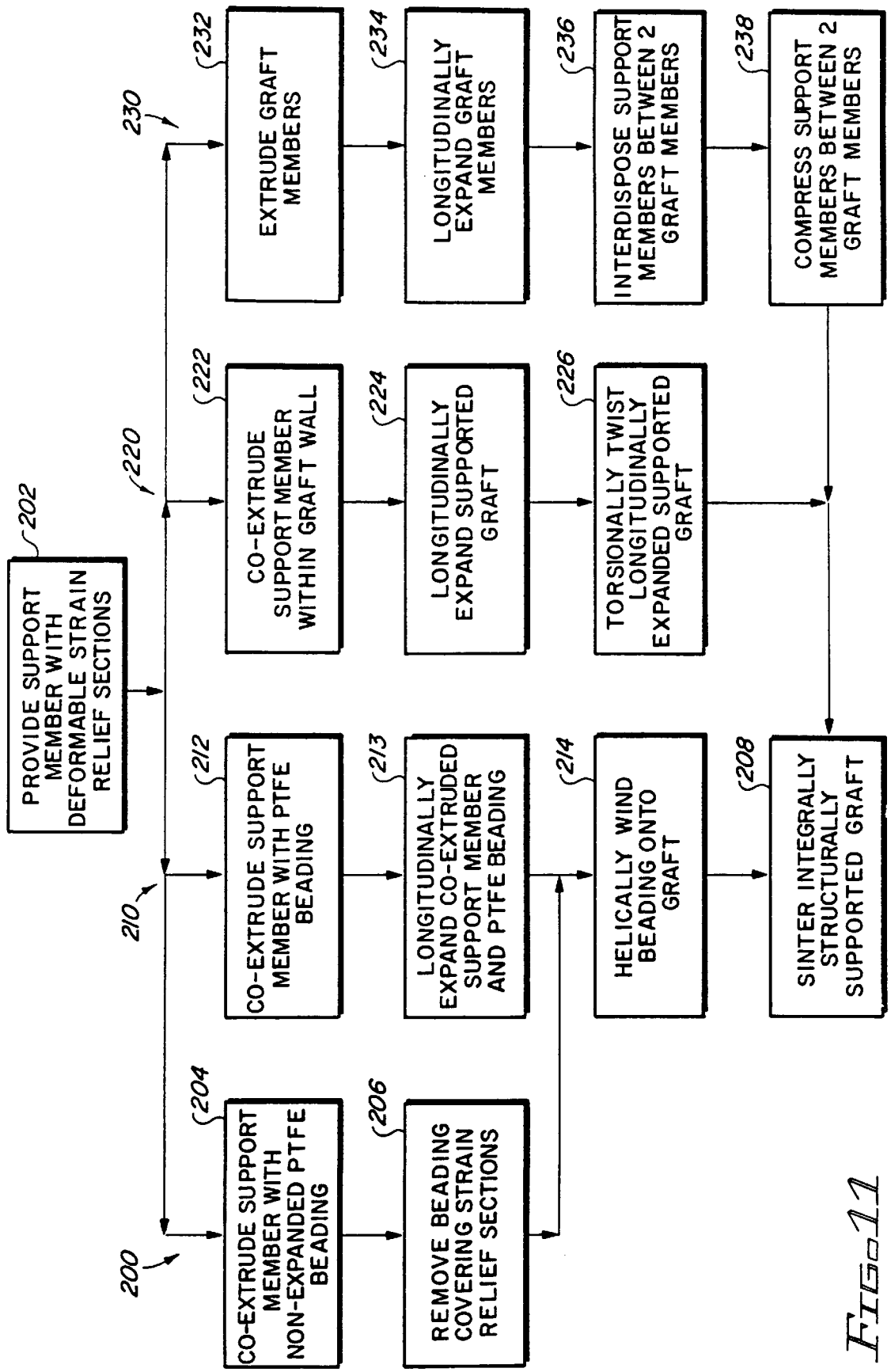

ENDOLUMINAL GRAFT WITH INTEGRAL STRUCTURAL SUPPORT AND METHOD FOR MAKING SAME

BACKGROUND OF THE INVENTION

The present invention relates generally to an intraluminal graft having an integral structural support which supports the intraluminal graft in an open condition and a method for making the inventive intraluminal graft. The integral structural support enhances dimensional stability of the graft, provides radial strength against radial constriction or collapse, yet permits radial expansion of the graft and facilitates intraluminal anchoring of the graft into the tissue defining an anatomical passageway. The integrally structurally supported endoluminal graft of the present invention includes a structural support integrally coupled to the graft and which has a plurality of strain relief segments. The strain relief segments, upon cumulative longitudinal deformation, delimit an upper limit of longitudinal and/or radial expansion of the graft itself.

The current trend is toward minimally invasive surgical procedures. Laparoscopic, endoscopic and percutaneous catheterization procedures have permitted surgeons to treat a broad spectrum of diseases and disorders while reducing body trauma, using local anesthesia, and decreasing patient pain and recovery time. Endovascular procedures such as percutaneous transluminal angioplasty (PTA) to treat vascular occlusive diseases, abdominal aortic aneurysm exclusions or peripheral aneurysmal exclusions are examples of minimally invasive interventional cardiovascular applications which have gained popularity. The present invention may be used with other endoscopic or percutaneous catheterization procedures for treating occlusive disorders in other anatomical passageways, including, but not limited to biliary ducts, ureters, urethras, fallopian tubes, etc. or to create shunts to restore blood flow, such as a transjugular intrahepatic portosystemic shunt (TIPS).

The present invention relates to various embodiments of an intraluminal graft, preferably made from longitudinally expanded polytetrafluoroethylene (ePTFE), which incorporate a structural member within or adjacent to the graft wall. In accordance with the preferred embodiment of the invention, a wire or ribbon member, fabricated of either metal or plastic, is incorporated either directly into the wall of the graft or into beading bonded to the graft. The structural member includes strain relief sections which permit both radial and longitudinal expansion of the graft. The structural member may further include tissue anchors comprising barbs or barb-forming sections distinct from the strain relief sections, or the strain relief sections may, themselves, act as the tissue anchors to anchor the graft to the anatomical passageway tissue.

The object of the present invention is to provide an structurally supported intraluminal graft useful as an endovascular graft which can be radially expanded in vivo, similar to endovascular stents described in U.S. Pat. No. 4,733,665 issued to Palmaz and U.S. Pat. No. 4,580,568 issued to Gianturco, which are well known in the art and which are currently being employed in many endovascular applications. The purpose of the present invention is to provide means which function to provide radial reinforcement for the graft, permitting radial expansion thereof, and which permits affixing the graft within an anatomical passageway such as a blood vessel.

Several strengthened or reinforced, yet radially compliant graft structures have been described in the art. For example, the Pinchuk patent, U.S. Pat. No. 4,629,458, discloses a tubular graft with an internal support layer. A silicone mandrel is coated with a fluid polymer and then helically wrapped with a monofilament polymer. The helical wrap may, alternatively, be positioned within the wall of the graft.

The Wall patent, U.S. Pat. No. 5,192,307 describes a radially expandable compliant prosthesis having metal springs embedded into the wall of the prosthesis. The prosthesis comprises a stent including a wall with a hook and hook means. The stent comprises a network of stainless steel or woven plastic covered by a plastic material. A plurality of circumferential ribs are placed about the stent to engage the arterial walls and prevent the inadvertent movement of the stent.

The Schwartz et al. patent, U.S. Pat. No. 5,282,823, describes a stent comprising a cylindrical body having a plurality of substantially helical metal elements joined together with a polymeric film extending between adjacent helical metal elements. The polymeric film has strain relief sections consisting of slits or cuts in the film between adjacent helical elements. The helical elements allow flexing of the stent along its longitudinal axis.

The Palmaz patent, U.S. Pat. No. 4,776,337, describes an expandable intraluminal composite graft comprising a tubular shaped member, comprising intersecting elongate members, and a biological inert coating placed over the tubular shaped member.

The Tessmann et al. patent, U.S. Pat. No. 5,167,614, describes a prostatic stent comprising a coiled rigid sheet, which may be expanded, and a plurality of hook like projections on the outer wall of the coil for anchoring the stent to the wall of a body passage. However, a grasping tool is required to expand and anchor the stent.

Other grafts attempt to replicate the inherent compliance of blood vessels. For example, the Kira patent, U.S. Pat. No. 4,857,069 discloses a composite artificial vessel having compliance and stress strain curves which approximate those of an actual blood vessel. The artificial vessel is made by coating a mandrel with an elastomer solution having a pore-forming agent and/or an elastomer solution having a cloud point, and immersing the coated mandrel into a coagulating liquid. The resulting artificial vessel has a porosity and compliance similar to a blood vessel.

SUMMARY OF THE INVENTION

It is a principal object of the present invention to provide a graft with an integrated structural support which provides radial dimensional stability to the graft and permits radial expansion of the graft.

It is a further object of the present invention to provide an expanded polytetrafluoroethylene endovascular graft having an integral structural support which provides dimensional stability to the graft, permits radial expansion of the graft and enhances graft patency within a blood vessel.

It is yet a further object of the present invention to provide an endoluminal structurally supported graft capable of both longitudinal and radial expansion.

It is a still further object of the present invention to provide an endoluminal structurally supported graft in which the structural support comprises strain relief sections having degrees of strain relief which are proportional to a predetermined final radial or longitudinal dimension of the graft.

It is still a further object of the present invention to provide an endoluminal structurally supported graft in which the structural support includes barb-forming sections which radially project outwardly from the central axis of the graft during radial expansion of the graft and which aid in anchoring the graft within an anatomical passageway.

It is still a further object of the present invention to provide a method for making a radially and longitudinally expandable structurally supported graft in which the structural support is integral with the wall of the graft, or is integrally bonded to an inner or outer wall surface of the graft.

It is still a further object of the present invention to provide a method for making a graft having an integral structural support which is incorporated into a beading associated with the graft wherein the integral structural support is capable of both longitudinal and radial expansion in order to fix or anchor the graft within a blood vessel.

A first embodiment of the graft having an integral structural support includes a tubular graft member, preferably comprised of ePTFE, a beading concentrically associated with the tubular member, and a structural support contained within the beading which comprises at least one of a rod or ribbon member having a plurality of strain relief sections. The beading is preferably comprised of non-expanded PTFE and the structural support is preferably comprised of metal or plastic. The structural support is a wire or ribbon that is preferably co-extruded within the non-expanded PTFE beading. The beading may be helically wound onto the ePTFE tubular member or placed onto the ePTFE tubular member in discrete rings on either the interior or exterior surface of the ePTFE tubular member. The beading is then secured onto the graft sintering the helically beaded graft at or above the crystalline melt point of polytetrafluoroethylene to bond the beading to the underlying ePTFE graft.

The structural support of this embodiment incorporates sectional or continuous strain relief segments, in the form of interspersed sections of reduced thickness, to allow for the radial dilatation of the graft. Radial dilatation of the structurally supported graft is facilitated by removing portions of the beading which encapsulate the strain relief sections of the structural support to expose the strain relief sections. To protect against over dilatation, the maximum quantum of strain relief is proportional to the final radial dimension that is required for the graft. Further, the structural support member may further comprise a plurality of barb-forming sections which form outwardly projecting barb members which extend outward from the support structure upon radial expansion of the graft.

For purposes of all preferred embodiments of the present invention, it will be understood that radial expansion of the graft is accomplished by imparting an outwardly directed radial force away from the central longitudinal axis of the structurally supported graft. It will be further understood that, because the structural support member is either helically wound or is provided as ring structures, the structural support member has a substantially radial orientation relative to the central longitudinal axis of the structurally supported graft. Thus, the radially oriented force relative to the central longitudinal axis of the graft is also a longitudinally-oriented force relative to the structural support member.

A second embodiment of the integral structural support graft includes a tubular member, preferably comprised of ePTFE, a beading concentrically associated with the tubular member which is also comprised of ePTFE, and a structural support contained within the beading which comprises at least one of a rod or ribbon having a plurality of strain relief sections. The structural support is preferably comprised of metal or plastic and is in the shape of a wire or ribbon capable of being co-extruded within the ePTFE beading. Like the previously described second embodiment, the beading may be spiraled onto the ePTFE tubular member or placed onto the ePTFE tubular member in discrete rings on either the interior or exterior surface of the ePTFE graft. The beading is then secured onto the graft using conventional processing methods.

The strain relief sections may be of two types; one for accommodating the longitudinal expansion of the graft and one for accommodating the radial expansion of the graft. The strain relief sections may take the form of folded sections or sections which are cut out of the rod or ribbon member. For example, horizontally disposed cut outs, in the form of notches, which extend through the width of a ribbon member will allow the graft to be horizontally expanded. Vertically disposed cut outs which extend along the entire width of the ribbon member, but not through its entire thickness, will allow the graft to be radially expanded. Unlike the first embodiment which contains non-expanded PTFE beading, there is no need to remove the ePTFE beading from the strain relief sections associated with this embodiment. Instead, the beading will expand with the longitudinal strain relief sections. Further, like the previously described embodiment, the structural support of the second embodiment may include barb-like protrusions extending outward in the radial direction to anchor the graft to the vessel wall.

A third embodiment of the integral structural support graft includes a tubular member, preferably comprised of ePTFE and a structural support in the form of a wire or ribbon member co-extruded with PTFE to form a wire-like beading. The beading is then longitudinally expanded to yield an ePTFE covering surround the structural support. Manufacture of the structural support within the PTFE covering is done in a manner similar to that known in the wire insulation fabrication arts.

The beading containing the wire or ribbon member, or the structural support member itself without a bead covering, is directly extruded either in the external or internal surface of the ePTFE tubular member such that the beading containing the wire or ribbon member forms an integral part of the tubular member. A helical orientation of the structural support member is either imparted during extrusion, or after extrusion by rotating or twisting the expanded graft after loading it onto a mandrel prior to sintering. Like the previously described second embodiment, two types of strain relief sections are incorporated into the structural support; one which permits longitudinal expansion of the integral structural support graft and one which allows for the radial expansion of the integral structural support graft. The number of strain relief sections and the degree of strain relief afforded by the strain relief sections determines the longitudinal and the radial expansion ratios of the final structurally supported graft. Also, like all of the previously described embodiments, the structural support of this embodiment may further comprise a plurality of barb-forming sections in the structural support which are deformed during radial expansion to project away from the central axis of the graft to anchor the graft in the anatomical passageway.

A fourth embodiment of the integral structurally supported graft includes a wire or ribbon member, having strain relief sections, encapsulated between concentrically joined tubular ePTFE grafts. A first tubular ePTFE graft member is mounted onto a mandrel. At least one wire or ribbon member, with a plurality of strain relief sections which permit longitudinal expansion of the wire or ribbon member upon application of a longitudinally oriented force relative to the longitudinal axis of the wire or ribbon member, is applied to an outer surface of the first tubular ePTFE graft member, either as a helical winding or as ring structures, a second tubular ePTFE graft member is then concentrically positioned about the first tubular ePTFE graft member and covering the wire or ribbon member. Circumferential pressure is applied to mechanically bond the first and second ePTFE tubular graft members to one another and encapsulate the wire or ribbon member therebetween. The first and second ePTFE tubular graft members may be formed either from tubular PTFE extrudates or from ePTFE planar sheets which are rolled into a tubular configuration upon one another with the structural support member interdisposed between adjacent ePTFE planar sheets. Like the above-described alternative embodiments of the integral structurally supported graft, the wire or ribbon support member may include a plurality of barb-forming sections in the support member which are deformed during radial expansion of the assembly to project away from the central axis of the graft and assist in anchoring the graft to adjacent tissue.

The method for making the integral structural support graft of the present invention includes the steps of 1) selecting or preparing a rod or ribbon member with strain relief sections; 2) co-extruding the rod or ribbon member with non-expanded PTFE beading; 3) removing longitudinal sections of the beading from the encapsulated strain relief sections; 4) helically winding the beading onto a tubular ePTFE graft member; and 4) mechanically bonding the beading to the surface of the graft member. Alternatively, the third step may be eliminated by co-extruding the rod or ribbon member with strain relief sections and the PTFE beading, longitudinally expanding the co-extruded structural support and PTFE beading, and then helically wound about and bonded to the surface of the graft member. The step of removing longitudinal sections of the beading from the strain relief sections is not required where the beading is expanded PTFE because the microporosity formed during longitudinal expansion of ePTFE will permit the strain relief sections to mechanically deform under the influence of the applied load and reposition within the ePTFE material matrix.

The integral structural support graft of the present invention may also be formed by extruding the co-extruded structural support alone, or with a beading directly with the ePTFE graft member. Further, the process for making the integral structural support graft may include extruding the structural support directly into the internal surface, external surface, or wall of the ePTFE graft member.

BRIEF DESCRIPTION OF THE DRAWINGS

FIG. 1 is a partial perspective view of a first embodiment of the integral structural support graft of the present invention showing the beading cut away from the strain relief sections of the integral structural support.

FIG. 1A is a perspective view of a section of co-extruded rod/wire member and beading with the beading cut away from the strain relief section of the rod/wire member shown in phantom.

FIG. 2 is a partial perspective view of a ribbon shaped structural support co-extruded into beading, which is later spiraled or placed in concentric rings around a tubular graft to form a second embodiment of the integral structural support of the present invention, with the ribbon shaped structural support shown in phantom.

FIG. 3A is a top elevational view of a zig-zag fold embodiment of the integral structural support of the present invention shown in its unexpanded condition.

FIG. 3B is a top elevational view of the zig-zag fold embodiment of the integral structural support of the present invention shown in FIG. 3A in its longitudinally expanded condition.

FIG. 4A is a top elevational view of a U channel stamp embodiment of the integral structural support of the present invention in its unexpanded condition.

FIG. 4B is a top elevational view of the U channel stamp embodiment of the integral structural support of the present invention shown in FIG. 4A in its longitudinally expanded condition.

FIG. 5A is a top elevational view of a square stamp embodiment of the integral structural support of the present invention in its unexpanded condition.

FIG. 5B is a top elevational view of the square stamp embodiment of the integral structural support of the present invention shown in FIG. 5A in its longitudinally expanded condition.

FIG. 6A is a top elevational view of a diamond stamp embodiment of the integral structural support of the present invention in its unexpanded condition.

FIG. 6B is a top elevational view of the diamond stamp embodiment of the integral structural support of the present invention shown in FIG. 6A in its longitudinally expanded condition.

FIG. 7A is a top elevational view of a "V" groove stamp embodiment of the integral structural support of the present invention in its unexpanded condition.

FIG. 7B is a top elevational view of the "V" groove stamp embodiment of the integral structural support of the present invention shown in FIG. 7A in its longitudinally expanded condition.

FIG. 8 is a perspective view of a third embodiment of the integral structural support graft of the present invention shown in its longitudinally oriented configuration prior to helically displacing the co-extruded beading and structural support about its central axis.

FIG. 9A is a perspective view of a fourth embodiment of the integral structural support graft of the present invention, in an unexpanded state, showing the structural support contained within the wall of the graft.

FIG. 9B is a perspective view of the fourth embodiment of the integral structural support graft of the present invention shown in FIG. 9A, in a radially expanded state.

FIG. 9C is a side elevational view of the fourth embodiment of the integral structural support graft of the present invention illustrating a first helical winding pattern for the structural support member.

FIG. 9D is a side elevational view of the fourth embodiment of the integral structural support graft of the present invention illustrating a second helical winding pattern for the structural support member.

FIG. 10 is a perspective of an integral structural support encapsulated within a planar film of ePTFE which is rolled into the tubular configuration as shown in FIGS. 9A and 9B.

FIG. 11 is a flow chart showing the processes for making the preferred embodiments of the integral structurally supported graft of the present invention.

DETAILED DESCRIPTION OF THE PREFERRED EMBODIMENTS

The accompanying Figures illustrate the four preferred embodiments of the inventive graft with integral structural support and the method of making the inventive with integral structural support. A first preferred embodiment of the invention is a graft supported with helically wound solid unexpanded polytetrafluoroethylene (PTFE) beading co-extruded with a strain-relived radiopaque support. A second preferred embodiment of the invention is a graft supported with helically wound expanded polytetrafluoroethylene (ePTFE) co-extruded with a strain-relieved radiopaque support. A third preferred embodiment of the present invention includes a graft supported with integral beading, in which a strain-relieved radiopaque support is co-extruded with the integral beading. Finally, a fourth preferred embodiment of the present invention includes a radiopaque structural support member encapsulated between concentric tubular ePTFE graft members.

Various configurations of strain relief sections on the wire or ribbon support member may be employed which are functionally equivalent to the particular embodiments of the strain relief sections described herein. Thus, while particular reference is made to individual configurations of the strain relief sections in the description of the preferred embodiments of the present invention, use of the term "strain relief section" is intended to mean any means which permits longitudinal plastic deformation of the support member, i.e., beyond the elastic limit of the material of the support member and beyond the elastic limit of the particular dimensional configuration of the support member, without causing mechanical failure and breakage of the support member.

First Embodiment

In accordance with the first preferred embodiment of the present invention, and with particular reference to FIGS. 1 and 1A, an integrally supported tubular graft 10 comprises a tubular graft member 12 having a first open end 14, a second open end (not shown), and a wall having a luminal surface 16 and an abluminal surface 18 which are separated by a wall thickness 20. The luminal surface 16 of the tubular graft member 12 defines a graft lumen 22 which permits fluid flow therethrough. The tubular graft 10 is preferably made of polytetrafluoroethylene extruded by ram extrusion of a polytetrafluoroethylene-lubricant billet through an extrusion die to form a tubular extrudate, which is then longitudinally expanded and sintered at or above the crystalline melt point of polytetrafluoroethylene as is well known in the art. The resulting longitudinally expanded polytetrafluoroethylene (ePTFE) has a characteristic microporous node and fibril microstructure.

Beading 24, covering a longitudinally extending support member 30, concentrically positioned within the beading 24 is helically provided about the tubular shaped member 12 and is preferably placed about the abluminal surface 18 of the tubular graft member 12. The beading 24 and the structural support 26 are preferably co-extruded in accordance with methods of making insulated electrical wire known in the wire making arts. The support member 26 preferably comprises a wire or ribbon-shaped member having a plurality of strain relief sections 30 which permit elongation of the support member 26 under the influence of a longitudinally applied force. As illustrated in FIGS. 1 and 1A, support member 26 comprises a wire-like member 28 covered by the co-extruded beading 24 and having a plurality of strain relief sections 30 periodically positioned along the longitudinal length of the support member 26. The strain relief sections 30 consist of regions of the wire-like member 28 uncovered by the co-extruded beading 24 and weakened relative to the covered regions of the wire-like member 28, such as by having a narrowed diameter relative to the covered regions of the wire-like member 28. The strain relief sections 30 longitudinally deform under the influence of a longitudinally applied load, such as by the relatively weakened regions elongating. The strain relief sections 30 may also be formed by selectively weakening or hardening longitudinal regions of the wire-like member 28 and without altering their dimensional profile. For example, a length of wire-like member 28 may be exposed to high temperatures at periodic intervals along its length to alter the metallurgical properties, and hence, the mechanical properties of the treated regions. These strain relief sections 30 are preferably uncovered by the beading 24, which is co-extruded with the wire-like member 28. The beading 24 covering the strain relief sections 30 may be removed by selective application of thermal energy, gamma irradiation, chemical etching, or by mechanical means such as manually or mechanically cutting the beading 24 from the strain relief section 30. The wire-like member 28 is preferably comprised of a metal. Suitable metals are Nitinol, stainless steel, titanium, tantalum and gold alloys. The beading 24 is preferably non-expanded sintered PTFE.

The beading 24 and the wire-like member 28 coextruded therewith are preferably helically wound or positioned as circumferential rings about the outer surface 18 of the tubular graft member 12 and mechanically bonded to the tubular graft member 12. Mechanical bonding is accomplished either by use of a biocompatible melt thermoplastic, a biocompatible adhesive such as silicone, or by sintering the beading 24 to the graft member 12.

The integrally structurally supported graft 10 is preferably delivered percutaneously on an angioplasty balloon catheter or using a delivery catheter having a sheath covering the graft. When the integral structural supported graft is delivered to the desired endoluminal site, it is radially expanded in vivo, and the exposed strain relief sections 30 permit radial expansion of the tubular graft member 12. Upon radial expansion of the tubular graft member 12, the beading 24 will allow for the radial expansion of the tubular PTFE graft 12 and the corresponding beading 24.

Second Embodiment

A second preferred embodiment of the integral structural support of the present invention generally includes a tubular graft member comprised of ePTFE, a structural support member having a plurality of strain relief sections and an ePTFE covering for the structural support member. Unlike the first embodiment of the present invention, described above, in accordance with the second embodiment of the invention, the structural support member remains fully covered by the ePTFE covering. Because of the microporous microstructure of ePTFE, the need to remove sections of the structural support member covering to permit longitudinal expansion of the structural support member, is avoided. The structural support member is preferably co-extruded with the ePTFE covering, as is well known in the wire-making arts. At least two types of strain relief sections are provided on the structural support member, one strain relief section permits a greater degree of longitudinal expansion of the structural support member than the second strain relief section. In this manner, both longitudinal expansion of the base structurally supported graft and radial expansion of the base structurally supported graft are accommodated.

An example of the co-extruded ribbon member 46 and ePTFE beading 48 which comprises part of the second embodiment of the integral structural support graft of the present invention is shown in FIG. 2. The strain relief sections may exhibit many forms. In FIG. 2, sections of the ribbon member are have altered profiles which form strain relief sections. More specifically, a first set of strain relief sections 50 comprise horizontally disposed recesses which extend through the width of a ribbon member thereby allowing the graft to be horizontally expanded. A second set of strain relief sections 52 comprise vertically disposed recesses which extend along the entire width of the ribbon member, but not through its entire thickness, thereby allowing the graft to be radially expanded. Further, the ribbon member 46 of the second embodiment may include a third set of strain relief sections 54 which form barb-like protrusions extending outward in the radial direction upon expansion of the integral structural support graft to anchor the graft to the vessel wall.

Third Embodiment

A third embodiment of the integrally structurally supported graft 100 is shown in FIG. 8. Integrally structurally supported graft 100 consists generally of a tubular graft member 102, preferably comprised of ePTFE, having at least one of a plurality of integral, monolithic rib structures 106 formed on and protruding outwardly from an abluminal surface 114 of the tubular graft member 102 and a structural support member 104 carried within and covered by the at least one rib structure 106. The method of extruding the tubular graft member 102 having at least one of a plurality of integral, monolithic rib structures 106 is preferably that disclosed and described in International Application Publication No. WO 9510247, published Apr. 20, 1995, which is the subject of common ownership with the present application, and is hereby incorporated by reference thereto. The tubular graft member 102 has a first open end 108, a second open end 110, an interior or luminal surface 112 defining graft lumen 116, and the abluminal or exterior surface 114. Structural support member 104 comprises at least one of a plurality of strain relief sections which permit both longitudinal and radial expansion of integrally structurally supported graft 100. Structural support member 104 and tubular graft member 102, with integral rib structures 106, are preferably co-extruded simultaneously as is well known in the wire-making art. The resulting co-extrudate, depicted in FIG. 8, is characterized by a tubular graft member 102 having at least one of a plurality of longitudinal rib structures 106 bearing the structural support member 104 therein. The co-extrudate is first processed by longitudinally expanding the co-extrudate, with a first of a plurality of strain relief sections borne on the structural support member 104 accommodating longitudinal expansion of the tubular graft member 102 and the integral rib structures 106. After longitudinal expansion, a torsional force is applied to the tubular graft 102, integral rib structures 106 and structural support member 104 to cause a helical displacement of the tubular graft 102, integral rib structures 106 and the structural support member 104, the resulting structure appearing to have a helical winding of the rib structures 106 carrying the structural support member 104. While the torsional force is maintained by restraining the opposing open ends 108, 110 of the tubular graft member 102, the co-extrudate is sintered at or above the crystalline melt point of PTFE and allowed to cool.

Alternatively, the structural support member 104 and tubular graft member 102, with integral rib structures 106, are simultaneously co-extruded while being rotated within the ram extruder, as described in International Application Publication No. WO 9510247, which is hereby incorporated as teaching an extrusion method in which a PTFE billet rotated while ram extruding the billet into a tubular member, and for longitudinally expanding the issuing extrudate while maintaining rotational movement of the extrudate. The resulting co-extrudate is characterized by a tubular graft member 102 having at least one of a plurality of longitudinal rib structures 106 bearing the structural support member 104 therein, helically disposed on either the inner, luminal surface of the resulting graft or on the outer, abluminal surface of the resulting graft.

Fourth Embodiment

Finally, a structurally supported graft 120 having a structural support member carried within the wall of the tubular graft member is provided in accordance with a fourth preferred embodiment of the present invention. As illustrated in FIGS. 9A and 9B, a structural support member 122, shown in phantom, is carried within the wall of the tubular graft member 124 residing between abluminal wall surface 126 and the luminal wall surface 128 of the graft member 124. The structural support member 122 having a plurality of strain relief sections, may be co-extruded with the graft member 124, then longitudinally expanded and sintered coincidental with the graft member 124, or may be interdisposed between at least two adjacent, concentrically joined unsintered longitudinally expanded graft members 124, depicted by phantom line 125, and sintered coincidental with the at least two graft members 124. In order to maintain adequate circumferential and longitudinal dimensional stability in the structurally supported graft 120, it is preferable that the structural support member 124 be formed as an open helical winding or as co-axial ring structures arrayed alone the longitudinal axis of the structurally supported graft 120. FIG. 9A illustrates the structurally supported graft 120 in its diametrically and longitudinally unexpanded state, while FIG. 9B illustrates the structurally supported graft 120 in its longitudinally and diametrically expanded state.

Where the structural support member 122 is encapsulated between at least two adjacent, concentrically joined graft members 124, depicted by phantom line 125, it is preferable to ram extrude the at least two tubular graft members 124 into tubular extrudates and then longitudinally expand the tubular extrudates to form unsintered tubular graft members 124, in accordance with well known processes for making tubular longitudinally expanded polytetrafluoroethylene. The at least two tubular graft members 124 may be selected to have the same or substantially the same material properties or may have different and distinct material properties from one another. For example, the outer tubular graft member 124 may be made to have higher internodal distances (IND) and, therefore, have a greater porosity and lower density than the inner tubular graft member 124, or the inner tubular graft member 124 may have a greater wall thickness than the outer graft member to permit the structural support member 122 to helically wound about or circumferentially positioned about the inner tubular graft member and embedded into the inner graft member's outer wall surface by application of positive pressure, before concentrically joining the outer tubular graft member 124 to the inner tubular graft member 124. Various other material properties of polytetrafluoroethylene grafts, such as water entry pressure, ethanol bubble point, suture retention strength, longitudinal tensile strength, node and fibril dimension, and the like, may be selected and varied in accordance with known methods of processing polytetrafluoroethylene, as desired.

The integrally structurally supported graft 120 of the present invention is made by mounting a first tubular graft member 124 upon a mandrel, coupling at least one of a plurality of structural support members 122 to the first tubular graft member 124, concentrically mount a second tubular graft member 124 over the at least one of a plurality of structural support members 122 and the first tubular graft member 124, apply circumferential pressure to the resulting assembly to mechanically bond the first and second tubular graft members 124 to one another about the at least one structural support member 122, and sinter the resulting assembly at or above the crystalline melt point of PTFE. It is important that the at least one structural support member 122 be coupled in such a manner as to provide dimensional stability to the resulting structure in both the radial and longitudinal axes of the structurally supported graft 120. It has been found preferable to configure the structural support member 122 as either a helical winding about and along the longitudinal extent of the first tubular graft member 124 or as ring structures interconnected by helically wound sections of the structural support member 122.

The resulting structure is an encapsulated integrally structurally supported graft 120 in which the graft members 124 are made of ePTFE and characterized by a microporous material matrix of nodes interconnected by fibrils, surrounding the structural support member 122. Where the at least one of a plurality of structural support members are oriented substantially circumferentially relative to the first and second tubular graft members 124, the encapsulated structural support members 122 are capable of longitudinal expansion by the deformation of the plurality of strain relief sections upon radial expansion of the structurally supported graft 120. As noted above, circumferential positioning of the structural support members 122 may be accomplished either by helically winding or radially winding the structural support members 122 about at least a portion of the longitudinal length of the first tubular graft member 124. In this manner, radial expansion of the structurally supported graft 120 causes contemporaneous deformation of the microporous material matrix of the first and second tubular graft members 124, with the node-fibril microstructure being deformed relative to its non-radially expanded state, and deformation of the encapsulated structural support members 122.

As noted above, the structural support member 122 may be helically wound or formed as ring structures about an outer surface of the first or inner tubular graft member 124 prior to covering with the second, or outer tubular graft member 124. Various other winding configurations for the structural support member 122 may be employed to optimize the dimensional stability of the resulting integrally structurally supported graft 120. FIGS. 9C and 9D illustrate two alternative helical winding patterns for the structural support member 122 which provide adequate longitudinal and radial dimensional stability to the integrally structurally supported graft 120, while still permitting the integrally structurally supported graft 120 to be radially expanded. Common to each of the two alternative winding patterns for the structural support member 122 are the features of 1) a continuous winding and 2) a plurality of ring structures formed on the outer surface 128 of the first graft member 124 at spaced-apart intervals along the longitudinal axis of the first graft member 128. A first winding pattern for the structural support member 122 is illustrated in FIG. 9C. In accordance with this first winding pattern, the structural support member 122, having a plurality of strain relief sections (not shown), is wound about an outer surface 128 of the first graft member 124 at one end thereof with high frequency windings to create closely adjacent helical windings, thereby forming a ring structure 135. After a first ring structure 135 is formed, the winding frequency is reduced to create a low pitch angle section 137 of the structural support member 122. The low pitch angle sections 137 of the structural support member interconnect adjacent pairs of ring structures 135 along the longitudinal axis of the structurally supported graft 120. A second winding pattern for the structural support member 122 is illustrated in FIG. 9D. In accordance with this first winding pattern, the structure support member 122, having a plurality of strain relief sections (not shown) is wound about an outer surface 128 of the first graft member 124, to create a first ring structure 137 adjacent one end of the first graft member. The first ring structure 137 is formed of closely spaced, high frequency helical windings. After the first ring structure 137 is formed, the helical winding pattern is interrupted and a straight section 138, oriented parallel to the longitudinal axis of the first graft member 124 is formed. The straight section 138 of the structural support member 122 interconnects an adjacent second ring structure 137 and successive adjacent pairs of ring structures 137 along the entire longitudinal axis of the first tubular graft member 134. Successive straight sections 138 may be formed in longitudinal alignment with one another at a given radial position on the circumference of the first tubular graft member 124, or may be radially offset from one another, i.e., at different radial positions on the circumference of the first tubular graft member 124. The longitudinal flexibility, i.e., the flexion characteristics in the longitudinal axis, of the resulting integrally structurally supported graft 120 can be controlled by altering the position of the plurality of straight sections 138 relative to one another or the low pitch angle sections 137 relative to one another.

It will be appreciated, by those skilled in the art, that the tubular graft members 124 may be made by ram extruding a compressed preformed billet of PTFE with an extrusion aide and ram-extruding the preformed billet through a die to yield a PTFE extrudate. To obtain a tubular graft member 124, the extrusion die may either be a circular die which receives a circular mandrel therethrough to obtain a tubular extrudate, or may be a slotted die to obtain a planar extrudate. Where a tubular extrudate is obtained by ram extruding a compressed billet, made of PTFE and lubricant, through an annular opening formed by the circular die opening and an extrusion mandrel, the tubular extrudate is longitudinally expanded to form the tubular graft members 124. However, where a planar extrudate is desired, the planar extrudate is obtained by ram extruding a compressed billet, made of PTFE and lubricant, through a rectilinear opening formed in the extrusion die. The planar extrudate is then longitudinally expanded to form an ePTFE sheet material. As illustrated in FIG. 10, in which the elements are denoted by reference numerals common with those for analogous elements in FIGS. 9A and 9B, the tubular integrally structurally supported graft 120 may be made from one or more planar ePTFE sheets 124 which are rolled about a forming mandrel to impart a tubular configuration to the ePTFE sheets 124.

Alternative methods of forming the integrally structurally supported ePTFE sheet material are contemplated by the present invention. First, the at least one structural support member 122 may be co-extruded with a planar extrudate and longitudinally expanded with the co-extruded PTFE. Second, the at least one structural support member 122 may be interdisposed between adjacent first and second ePTFE sheet graft members 124, denoted by phantom line 125, and the first and second ePTFE sheet graft members 124 compressed to mechanically bond the first and second ePTFE sheet graft members 124 to one another around the at least one structural support member 122. The resulting structurally supported planar graft assembly 120 is then rolled, preferably about a mandrel, along the longitudinal axis of the structural support members, as denoted by arrow 128, such that the opposing ends 127, 129 of the planar graft member 124, having the at least one structural support member 122 terminating therewith, are brought into proximity with one another, preferably abutting one another or overlapping one another. Alternatively, the structurally supported planar graft assembly 120 may be rolled about a mandrel in a diagonal orientation such that the at least one structural support member 122 assumes a helical winding pattern. The resulting seam formed between the proximate opposing ends 127, 129 or between lateral edges of the structurally supported sheet graft member 124, depending upon the orientation of rolling, are then preferably heat sintered to one another using either a PTFE tape or a fluoroethylpolypropylene (FEP) tape, or by heat sintering the overlapping opposing ends 127, 129 to one another.

One particular advantage of forming the tubular structurally supported graft 120 by encapsulating the structural support member 122 between planar ePTFE sheets 124, as depicted in FIG. 10, is that the material properties of the planar ePTFE sheets 124 may be different from one another. The planar ePTFE sheets 124 may be selected to have the same or substantially the same material properties or may have different and distinct material properties for one another. For example, a first planar ePTFE sheet 124 may be made to have higher internodal distances (IND) and, therefore, have a greater porosity than the second planar ePTFE sheet 124, or the first planar ePTFE sheet 124 may have a greater wall thickness than the second planar ePTFE sheet 124 to permit the structural support member 122 to embed a greater extent into the thicker first planar ePTFE sheet 124, upon application of positive pressure, before the first and second planar ePTFE sheets 124 to one another. Various other material properties of polytetrafluoroethylene grafts, such as water entry pressure, ethanol bubble point, suture retention strength, longitudinal tensile strength, node and fibril dimension and orientation, and the like, may be selected and varied in accordance with known methods of processing polytetrafluoroethylene, as desired. To increase the hoop strength of the resulting tubular structurally supported graft 120, the fibril orientations of the first and second ePTFE sheets 124 may be oriented perpendicular to one another during assembly. Because the fibril orientation of expanded polytetrafluoroethylene is parallel to the direction of expansion, uniaxially expanded PTFE exhibits fibrils extending parallel to the direction of expansion, while biaxially expanded PTFE exhibits fibrils extending parallel to each axis of expansion. Thus, it is desirable to position the fibril orientation of the first planar ePTFE sheet 124 perpendicular to the fibril orientation of the second planar ePTFE sheet 124, and encapsulating the structural support member 122 therebetween. The resulting structurally supported graft 120, after rolling into a tubular structure, sealing the seams and sintering the assembly, will exhibit dimensional stability in both the longitudinal and radial axes of the structurally supported graft 120 in a manner analogous to a biaxially expanded PTFE material.

FIGS. 3A and 3B through FIGS. 7A and 7B depict various configurations of the structural support members of the integrally structurally supported grafts of the first, second and third embodiments of the present inventions, described above, and depict the structural support member in its non-longitudinally expanded state and in its longitudinally expanded state. Each of the configurations incorporates at least one type of strain relief section. The strain relief sections preferably take the form of folded elements, plastic deformable sections, weakened sections or any equivalent section which permits longitudinal elongation of the structural support member while retaining the material integrity without separation of the material into discrete segments. At least one of the plurality of strain relief sections may include barb-forming segments which, upon longitudinal elongation of the structural support member, form outwardly projecting barbs which facilitate anchoring of the integrally structurally supported graft into the tissue defining the anatomical passageway. Radial expansion of the integrally structurally supported graft imparts a longitudinally oriented force to the structural support member, thereby deforming at least one type of the plurality of strain relief sections and longitudinally elongating the structural support member.

FIG. 3A illustrates a folded element configuration structural support member 60 in which a wire-like member is bent or otherwise formed, such as by stamping a planar material, or molding a moldable material, into a plurality of everted Z-shaped sections 62. FIG. 3B shows the folded element configuration structural support member 60 in its longitudinally expanded state. In its longitudinally expanded state, the Z-shaped sections 62 form pointed barbs 64 which project away from the central axis of the structural support member 60 and provided anchor points to anchor the integrally structurally supported graft within the tissue defining the anatomical passageway.

FIG. 4A illustrates another embodiment of the structural support member 66 having a generally U-shaped configuration and comprising a wire-like structural support member 66 bent or otherwise formed, such as by stamping a planar material or molding a moldable material, into a plurality of U-shaped sections 68, 70 having each linear member defining the U-shaped section 68, 70 assuming approximately a 90 degree angle relative to an adjacent linear member. Barb-forming members 72 may, optionally, be attached to or be an integral part of the structural support member 66 and project outwardly from at least one linear member of each U-shaped section 68, 70, but are co-planar and co-axial with the structural support member 66 when in its non-longitudinally expanded state, as illustrated in FIG. 4A. As illustrated in FIG. 4B, longitudinal expansion of the structural support member 66 causes longitudinal deformation of each of the plurality of U-shaped sections 68, 70 such that the linear members defining the U-shaped sections 68, 70 are deformed relative to one another and assume an obtuse angle, i.e., greater than 90 degrees, relative to an adjacent linear member of the U-shaped sections 68, 70 and the barb-forming members 72 project outwardly from the central axis of the structural support member 66.

FIG. 5A illustrates a square stamp embodiment of the structural support member 74 in accordance with the present invention. The square stamp structural support member 74 comprises a series of alternating closed square members 76 and open square members 78 which are connected to one another along a longitudinal axis of the structural support member 74 by connecting members 79. The structural support member 74 is preferably formed by die stamping a planar material into the square stamp configuration of the structural support member 74. Alternatively, the structural support member 74 may be made by molding a moldable material or deforming a flattened wire-like material into the configuration of structural support member 74. As illustrated in FIG. 5B, longitudinal expansion of the structural support member 74 causes linear deformation of the closed square members 76 and the open square members 78, with the open square members 78 opening and outwardly projecting barb-forming members 80 away from the longitudinal axis of the structural support member 74.

FIG. 6A illustrates a diamond stamp structural support member 82 in its non-longitudinally expanded state. The diamond stamp structural support member 82 comprises a linear series alternating closed diamond shaped members 84 and open diamond shaped members 86 interconnected along their longitudinal axis by a plurality of linear strut members 89. As illustrated in FIG. 6B, longitudinal expansion of the diamond stamp structural support member 82 causes the longitudinal deformation of the open 86 and closed 87 diamond shaped members, with the open diamond shaped members 87 deforming to outwardly project barb-forming open ends 88 of the open diamond shaped members 87 away from the longitudinal axis of the structural support member 82. The structural support member 82 is preferably formed by die stamping a planar material into the diamond stamp configuration of the structural support member 82. Alternatively, the structural support member 82 may be made by molding a moldable material or deforming a flattened wire-like material into the configuration of structural support member 82.

FIG. 7A illustrates a structural support member 90 formed of a plurality of longitudinally interconnected V-shaped members 92. Some of the V-shaped members 94 have a barb-forming member 96 attached at an apex of the V-shaped member 94, the barb-forming member 96 being oriented substantially parallel to the longitudinal axis of the structural support member 90 in its non-longitudinally expanded state. As illustrated in FIG. 7B, longitudinal expansion of the structural support member 90 causes the longitudinal deformation of each of the plurality of longitudinally interconnected V-shaped members 92, including the V-shaped members 94 having the barb-forming member 96 attached thereto. Upon longitudinal deformation of the structural support member 90, the plurality of V-shaped members 94 assume a flattened linear configuration, with the barb-forming members 96 projecting outwardly away from the longitudinal axis of the structural support member 90. As with the previously described embodiments, the structural support member 90 is preferably formed by die stamping a planar material, alternatively, the structural support member 90 may be made by molding a moldable material or deforming a flattened wire-like material into the configuration of structural support member 90.

In each of the foregoing described embodiments of the structural support member 30, 50, 60, 70, 80 and 90, described with reference to FIGS. 1–7B, the strain relief sections may be formed by obtaining or preparing a wire-like member, made of a ductile metal or plastic material, and selectively treating longitudinal sections of the wire-like member to obtain variable longitudinal mechanical properties in the wire-like member. The selective treatment of longitudinal sections of the wire-like member preferably include exposing the selected longitudinal sections to thermal energy, such as RF energy, laser energy, resistive heating, induction heating, gamma irradiation or the like to selectively harden or weaken sections of the wire-like member, thereby obtaining intermediate sections of the wire-like member which exhibit differential ductility and serve as the strain relief sections. Alternatively, longitudinal sections of the wire-like member may be selectively exposed to thermal, chemical or mechanical energy or to a source of radiation, such as x-ray, gamma ray or photon energy to define either a positive or negative image, with subsequent processing to etch sacrificial areas from the wire-like member, such as by photolithography or x-ray lithography, thereby dimensionally altering the transverse cross-sectional profile of the wire-like member. Examples of methods useful to remove sacrificial areas of the structural support member include laser etching, chemical etching, photolithography, x-ray lithography, mechanical cutting, machining, or equivalent methods.

Turning now to FIG. 11, the process for making the first 200, second 210, third 220 and fourth embodiments 230 of the integrally structurally supported graft of the present invention is set forth. The inventive process for making each preferred embodiment of the integrally structurally supported graft starts with step 202, which is providing a structural support member having a plurality of deformable strain relief sections periodically provided along a longitudinal length of the structural support member. The structural support member provided at step 202 is preferably selected from the various preferred embodiments for the structural support member described above with reference to FIGS. 1–7B. The process for making the first preferred embodiment 10 of the integrally structurally supported graft then includes the step 204 of co-extruding the selected support member with non-expanded polytetrafluoroethylene beading such that the support member is covered by non-expanded polytetrafluoroethylene. Longitudinal sections of the non-expanded polytetrafluoroethylene are then removed in step 206 to expose a plurality of the underlying strain relief sections. As noted above, removal of the longitudinal sections of the non-expanded polytetrafluoroethylene may be accomplished by a wide variety of methods, such as laser etching, chemical etching, mechanical cutting, or equivalent methods. The process for making the second preferred embodiment of the integrally structurally supported graft 210 entails providing a support member having at least two types of strain relief sections, a plurality of first strain relief sections having a degree of longitudinal deformability commensurate with the degree of longitudinal expansion to which the base structurally supported graft will be exposed, and a plurality of second strain relief sections having a degree of longitudinal deformability commensurate with the degree of radial expansion to which the base structurally supported graft will be exposed. The selected support member is then co-extruded at step 212 with a PTFE covering, and the PTFE covering and the support member are longitudinally expanded together at step 213 to obtain an ePTFE covering over the support member wherein the plurality of second strain relief sections are not deformed during longitudinal expansion. The process for making the first 200 and the second 210 preferred embodiments then share the common steps of helically winding either the PTFE covered support member with exposed strain relief sections or the ePTFE covered support member with unexposed strain relief sections about a tubular graft member at step 214 and sintering the resulting assembly under the presence of a circumferentially applied force to mechanically bond the covered support member to the tubular graft member.

The process of making the third 220 and the fourth 230 preferred embodiments of the invention involve different processing of the support member. The process of making the third 220 embodiment of the integrally structurally supported graft entails selecting a support member as in step 202 having at least two types of strain relief sections. The at least two types of strain relief sections include a plurality of first strain relief sections having a degree of longitudinal deformability commensurate with the degree of longitudinal expansion to which the base structurally supported graft will be exposed, and a plurality of second strain relief sections having a degree of longitudinal deformability commensurate with the degree of radial expansion to which the base structurally supported graft will be exposed. The selected support member is then co-extruded at step 222 with the graft member. The graft member is either extruded as a tubular shape or as a planar shape, with the selected support member being co-extruded within the graft wall or within an integral, monolithic rib member which protrudes outward from the graft member, as described in International Application Publication Number WO 9510247, published Apr. 20, 1995, which is commonly assigned to the assignee of the present application and which is hereby incorporated by reference as describing a graft member and process for making a graft member suitable for co-extrusion with the structural support member of the present invention. The resulting co-extrudate is then longitudinally expanded at step 224, in accordance with known method for longitudinally expanding polytetrafluoroethylene extrudates and may, optionally, be torsionally rotated at step 226 about its central axis to impart a helical winding to the support member and the wall of the graft member. The resulting co-extrudate is then sintered at step 208 while being longitudinally restrained.

The fourth embodiment 230 of the integrally structurally supported graft is made by first selecting a desired support member at step 202. Because the fourth embodiment 230 of the integrally structurally supported graft is an encapsulated variant, the support member need have only one type of strain relief section, i.e., one which will longitudinally expand to accommodate only radial expansion of the base graft member. It will be understood, however, that different types of strain relief sections may nonetheless be used. In accordance with the preferred method for making the fourth embodiment 230 of the integrally structurally supported graft, at least two graft members made of PTFE are extruded at step 232. The PTFE extrudates may be extruded as a tubular shape or may be extruded as a planar sheet of material. The PTFE extrudates are longitudinally expanded at step 234 in accordance with methods known in the art. The selected support member is then interdisposed between a pair of opposing ePTFE extrudates, preferably unsintered, which are then brought into intimate contact with one another surrounding the selected support member. It will be understood, of course, that the use of more than one support member interdisposed between a pair of opposing ePTFE extrudates is also contemplated by the present invention. Where unsintered tubular ePTFE extrudates are employed, it has been found desirable to mount a first unsintered tubular ePTFE extrudate onto a mandrel, circumferentially wrap the at least one support member, either as a helical wrap or as concentric ring structures, about the first unsintered tubular ePTFE extrudate. The second unsintered tubular ePTFE extrudate, preferably having a diameter greater than that of the first unsintered tubular ePTFE extrudate, is concentrically positioned over the first unsintered ePTFE tubular extrudate and the at least one support member. It is preferable to provide a second unsintered ePTFE tubular extrudate having an inner diameter which is greater than the outer diameter of the first unsintered ePTFE tubular extrudate in order to facilitate concentric joining of the first and second unsintered ePTFE tubular extrudates about the at least one support member. Circumferential pressure is then applied at step 238 to compress the at least one support member between the first and second unsintered ePTFE tubular extrudates to enhance mechanical bonding at the contact surface between the first and second unsintered ePTFE tubular extrudates. Where planar ePTFE extrudates are obtained, it is preferable to wrap a first one of the planar ePTFE extrudates, in its unsintered condition, circumferentially about a mandrel, then apply the at least one support member circumferentially about the exposed surface of the wrapped first planar ePTFE extrudate, then wrap the second one of the planar ePTFE extrudates about the first wrapped ePTFE extrudate and the at least one support member. It will be understood that when using planar ePTFE extrudates, it is desirable to provide an overlap seam to facilitate a complete circumferential closure of the graft member into a tubular configuration. The resulting assembly is then sintered at step 208 to obtain the integrally structurally supported graft capable of percutaneous delivery and co-incidental endoluminal radial expansion of the graft member and its integral support member.

Those skilled in the art will appreciate that the present invention provides an improved graft in the form of a graft having an integral structural support, in which the integral structural support has a plurality of strain relief segments which, upon cumulative longitudinal deformation, delimit an upper limit of longitudinal and/or radial expansion of the graft itself The present invention is particularly well-suited to any type of endoluminal application, such as widening occlusions, obstructions, strictures, or the like in anatomical passageways, such as the vasculature, biliary ducts, hepatic ducts, ureters, urethra, fallopian tubes, esophageal, or other similar anatomical passageways, or to exclude aneurysms in either the central or peripheral vasculature. Furthermore, the present invention may also be used to create passageways, such as shunts, between anatomical passageways. While the invention has been described with reference to preferred embodiments, the description is for illustrative purposes only and is not to be construed as limiting the scope of the invention. Various modifications and changes may be made by those skilled in the art without departing from the true scope of the invention as defined by the appended claims.

What is claimed is:

1. An endoluminal prosthesis, comprising:
    a tubular graft member having a first open end, a second open end, and a wall having an interior surface and an exterior surface which are separated by a wall thickness, the wall being located between the first and second open ends wherein the interior surface of the wall defines a lumen; and
    at least one structural support member coupled to the tubular graft member and containing a plurality of longitudinally deformable strain relief sections which permit contemporaneous longitudinal deformation of at least some of the plurality of strain relief sections and diametric expansion of the tubular graft members, wherein said strain relief sections are formed from a material having different mechanical properties than said tubular graft member.

2. The endoluminal prosthesis of claim 1, wherein said tubular graft member further comprises expanded polytetrafluoroethylene.

3. The endoluminal prosthesis of claim 1, wherein said structural support member further comprises a wire member.

4. The endoluminal prosthesis of claim 1, wherein the structural support is coupled to the tubular graft member by mechanical bonding with at least one of the exterior surface and within the wall thickness of the tubular graft member.

5. The endoluminal prosthesis of claim 1, wherein at least some of the plurality of strain relief sections further comprise barb-forming members which project barb members outwardly from a central axis of the support member upon diametric expansion of the tubular graft member.

6. The endoluminal prosthesis of claim 1, wherein the plurality of strain relief sections further comprise a plurality of first strain relief sections which permit longitudinal expansion of the tubular graft member and a plurality of second strain relief sections which permit diametric expansion of the tubular graft member.

7. The endoluminal prosthesis of claim 6, wherein the plurality of first and second strain relief sections each comprise longitudinal regions of the structural support member having differential moduli of elasticity.

8. The endoluminal prosthesis of claim 7, wherein the plurality of first strain relief sections further comprise recessed sections which extend into the structural support member substantially perpendicular to the longitudinal axis of the structural support member and the plurality of second strain relief sections further comprise recessed sections which extend in a direction substantially perpendicular to the longitudinal axis of the structural support member and substantially perpendicular to the direction of the first strain relief sections.

9. The endoluminal prosthesis of claim 1, wherein said structural support further comprises barb forming members which project away from the central longitudinal axis of the structural support member upon diametrical expansion of the tubular graft member.

10. The endoluminal prosthesis of claim 1, wherein the structural support member is covered by non-longitudinally expanded polytetrafluoroethylene and a plurality of the strain relief sections are exposed and uncovered by the non-longitudinally expanded polytetrafluoroethylene covering.

11. The endoluminal prosthesis of claim 1, wherein the structural support member is covered along its entire longitudinal axis by a longitudinally expanded polytetrafluoroethylene covering.

12. The endoluminal prosthesis of claim 1, wherein the tubular graft member further comprises at least one of a plurality of longitudinally extending rib structures projecting outwardly from the exterior surface of the tubular member, the at least one of a plurality of longitudinally extending rib structures is an integral and monolithic part of the wall thickness of the tubular member, and the structural support member is co-extruded within the at least one of a plurality of longitudinally extending rib structures.

13. The endoluminal prosthesis of claim 1, wherein the structural support member is co-extruded within the wall thickness of the tubular member.

14. The endoluminal prosthesis of claim 1, further comprising at least two micropororus expanded polytetrafluoroethylene tubular graft members and the at least one of a plurality of support members is interdisposed between the at least two microporous expanded polytetrafluoroethylene tubular graft members, the at least two microporous expanded polytetrafluoroethylene tubular graft members being in intimate contact with one another and substantially encapsulating the at least one of a plurality of support members therebetween.

15. The endoluminal prosthesis of claim 14, further characterized in that the at least two microporous expanded polytetrafluoroethylene tubular graft members have different porosity.

16. The endoluminal prosthesis of claim 14, further characterized in that the at least two microporous expanded polytetrafluoroethylene tubular graft members have node and fibril microstructures with the fibril orientation of the two microporous expanded polytetrafluoroethylene graft members being oriented substantially perpendicular to one another.

17. An integrally structurally supported graft, comprising:
an expanded polytetrafluoroethylene tubular graft member;

a beading bound about one of an outer and inner surface of the tubular member; and at least one structural support member at least partially retained within the beading, the at least one structural support member having a plurality of deformable strain relief sections which deform under the influence of a longitudinally-oriented load thereby extending the longitudinal length of the at least one structural support members wherein said structural support member is made of a material, having different mechanical properties than said tubular graft member.

18. The graft of claim 17, wherein the beading comprises one of expanded polytetrafluoroethylene and non-expanded polytetrafluoroethylene.

19. The graft of claim 17, wherein the at least one structural support member is comprised of one of a ductile plastic and a ductile metal material.

20. The graft of claim 17, wherein the beading is circumferentially bound to the outer surface of the tubular graft member.

21. The graft of claim 17, wherein the beading is integrally bound to at least one of an interior surface, exterior surface, and wall thickness of the tubular member.

22. The graft of claim 17, wherein the plurality of strain relief sections further comprise weakened sections of the structural support member.

23. The graft of claim 17, further comprising a plurality of uncovered strain relief sections.

24. The graft of claim 17, further comprising a plurality of barb-forming members on the structural support members, the plurality of barb-forming members being deformable to project away from the longitudinal axis of the structural support member upon longitudinal expansion of the structural support member.

25. The graft of claim 24, wherein said plurality of deformable strain relief sections further comprise a plurality of first strain relief sections and a plurality of second strain relief sections and wherein the plurality of first strain relief sections comprises weakened sections which extend into the structural support member substantially perpendicular to the longitudinal axis of the structural support member and the plurality of second strain relief sections further comprise weakened sections which extend in a direction substantially perpendicular to the longitudinal axis of the structural support member and substantially perpendicular to the direction of the first strain relief sections.

26. The graft of claim 17, wherein the structural support member is helically disposed relative to the tubular graft member.

27. The graft of claim 17, wherein the structural support member and the tubular graft member are co-extruded with one another.

28. A method for making a structurally supported graft comprising the steps of:
a) providing at least one structural support member having a plurality of longitudinally deformable inelastic strain relief sections;
b) circumferentially coupling the covered structural support member with a tubular graft member.

29. The method of claim 28, further including the step of co-extruding the at least one structural support member with a covering.

30. The method of claim 28, further including the step of encapsulating the at least one structural support member between at least two concentrically bound tubular graft members.

31. The method of claim 28, further including the step of removing sections of covering adjacent the plurality of longitudinally deformable strain relief sections prior to the co-extruding step.

32. A method for making a structurally supported graft comprising the steps of:
   a) providing a structural support member having a plurality of longitudinally deformable inelastic strain relief sections which permit longitudinal expansion of the structural support member under the influence of a longitudinally oriented load; and
   b) attaching the structural support member to a tubular graft member such that the plurality of strain relief sections are capable of longitudinal expansion under the influence of a longitudinally oriented load applied to the structural support member.

33. The graft of claim 17, wherein the plurality of strain relief sections further comprise a plurality of first strain relief sections which permit longitudinal expansion of the tubular graft member and a plurality of second strain relief sections which permit diametric expansion of the tubular graft member.

* * * * *